United States Patent [19]

Hawkins et al.

[11] Patent Number: 5,533,532
[45] Date of Patent: Jul. 9, 1996

[54] PERMANENT WAVE COMPOSITIONS AND METHODS

[75] Inventors: Geoffrey R. Hawkins, Langhorne, Pa.; Marvin E. Goldberg, Marlboro, N.J.

[73] Assignee: Revlon Consumer Products Corporation, New York, N.Y.

[21] Appl. No.: 494,504

[22] Filed: Jun. 26, 1995

[51] Int. Cl.⁶ ............................................. A45D 7/04
[52] U.S. Cl. ..................... 132/204; 132/202; 132/205; 132/200
[58] Field of Search ............................. 132/202, 204, 132/205, 206, 209, 200

[56] References Cited

U.S. PATENT DOCUMENTS

| | | | |
|---|---|---|---|
| 3,912,808 | 10/1975 | Sokol | 424/71 |
| 3,971,391 | 7/1976 | Bore et al. | 132/202 |
| 4,153,681 | 5/1979 | Shiba | 424/72 |
| 4,218,435 | 8/1980 | Shiba | 424/72 |
| 4,840,791 | 6/1989 | Matthews et al. | 132/202 |
| 4,859,459 | 8/1989 | Greiche | 424/71 |
| 4,963,349 | 10/1990 | Mathews | 424/72 |
| 5,085,860 | 2/1992 | Junino | 424/72 |
| 5,101,841 | 4/1992 | Crews et al. | 132/202 |
| 5,116,608 | 5/1992 | Yoshioka | 424/72 |
| 5,154,918 | 10/1992 | Maignan | 424/72 |
| 5,165,427 | 11/1992 | Borish | 132/204 |
| 5,208,014 | 5/1993 | Dubief | 424/71 |
| 5,223,252 | 6/1993 | Kolc | 424/72 |
| 5,225,191 | 7/1993 | de Labbey | 132/204 |
| 5,241,973 | 9/1993 | Salce | 132/205 |
| 5,332,570 | 7/1994 | Bergstrom et al. | 132/203 |
| 5,382,426 | 1/1995 | Nandagiri et al. | 132/204 |

*Primary Examiner*—Gene Mancene
*Assistant Examiner*—Pedro Philogene
*Attorney, Agent, or Firm*—Julie Blackburn

[57] ABSTRACT

A permanent wave composition having a pH of 6.0 to 7.0 comprising 10–20% by weight of a cysteamine reducing agent compound in an aqueous carrier, and a method and kit for permanent waving hair using the composition of the invention.

17 Claims, No Drawings

PERMANENT WAVE COMPOSITIONS AND METHODS

TECHNICAL FIELD

The invention is in the field of compositions used for permanent deformation of hair.

BACKGROUND OF THE INVENTION

Permanent waving of hair is accomplished by first arranging the hair in the desired configuration and applying a chemical which breaks the cystine sulfur to sulfur bonds found in the hair fibers. A second chemical, referred to as a neutralizer, is then applied to reform the sulfur to sulfur bonds. The resulting hair has become permanently waved.

Chemicals which are capable of breaking cystine sulfur to sulfur bonds are referred to as reducing agents. A wide variety of reducing agents exist; some of the more popular ones include thio compounds, sulfites and cysteine or cysteamine derivatives. Permanent waving can be carried out at either acid or alkaline pH, depending on the particular reducing agent selected. For example, acid permanent waves utilize reducing agents which are capable of curling hair at a pH of less than or equal to 7.0. These reducing agents generally have a low pKa value and exist predominantly in the dissociated form at a pH at or near neutral. On the other hand, alkaline permanent waves use reducing agents which have pKa values which are higher. For example, ammonium thioglycolate has a pKa of 10.4, thus it is effective as a waving agent only if the pH of the entire system is exceeds 9. Generally, the pKa of a reducing agent dictates the pH at which permanent waving must take place. If the pKa of a reducing agent is greater than 7.0, permanent waving efficiently takes place only at alkaline pH. Conversely, if the pKa of a reducing agent is less than 7.0, effective permanent waving only takes place at pH values less than or equal to 7.0.

It is well known that cysteamine or salts thereof are suitable reducing agents for permanent waving. The pKa of cysteamine is 9.0, meaning that it is most effective in breaking sulfur to sulfur bonds at alkaline pH. Cysteamine is generally used in conjunction with other reducing agents, such as thio compounds, because it is expensive and it is believed that the combination of cysteamine and thio compounds provides a synergistic effect. However, U.S. Pat. No. 5,260,054 teaches a permanent wave composition where cysteamine can be used alone as the sole reducing agent provided the pH of the composition falls within the narrow range of 7.8 to 8.8 and the cysteamine concentration of the composition ranges from 7.8 to 9.0 wt %. The '054 patent teaches that below pH 7.8 cysteamine performance is not adequate to permanent wave hair, and above a concentration of 9.0 wt % cysteamine, the product is too irritating to skin.

Applicants have most unexpectedly discovered that cysteamine based permanent waving can be very effectively accomplished at a pH range of 6.0 to 7.0 (far below the pKa of cysteamine), with compositions containing 10–20%, preferably 12–18% by weight cysteamine reducing agent. The compositions provide no discomfort or irritation, and more effectively permanent wave the hair than at alkaline pH and with lower concentrations of cysteamine.

SUMMARY OF THE INVENTION

The invention is directed to a permanent wave composition having a pH of 6.0 to 7.0 comprising 10–20% by weight of a cysteamine reducing agent compound in an aqueous carrier.

The invention is also directed to a method for permanent waving human hair comprising the steps of:

(a) applying to hair fibers arranged in a predetermined configuration a permanent wave composition having a pH of 6.0 to 7.0 comprising 10–20% by weight of a cysteamine reducing agent in an aqueous carrier, (b) applying heat to the hair treated with the composition of (a) for a period of time sufficient to cause rupture of the sulfur to sulfur bonds in the hair fibers, (c) applying a neutralizer to the hair fibers for a period of time sufficient to cause the sulfur to sulfur bonds to reform.

The invention is also directed to a kit for application of permanent waves to human hair comprising:

(a) a first container containing a permanent wave composition having a pH of 6.0 to 7.0 comprising 10–20% by weight of a cysteamine reducing agent compound in an aqueous carrier, and (b) a second container containing a neutralizer.

DETAILED DESCRIPTION

The term "permanent wave composition" means a composition containing a reducing agent capable of rupturing the cystine sulfur to sulfur bonds found in human hair fibers.

The term "neutralizing agent" or "oxidizing agent" means a composition capable of reforming the cystine sulfur to sulfur bonds which have been ruptured by the reducing agent.

The compositions of the invention have a pH ranging from 6.0 to 7.0, more preferably 6.5 to 7.0, and contain 10–20%, preferably 12–18% of a cysteamine reducing agent. The cysteamine reducing agent is cysteamine, cysteamine salts, or mixtures thereof. Cysteamine salts may be the hydrochloride, bromide, iodide, etc. The preferred cysteamine reducing agent is cysteamine hydrochloride. In the compositions of the invention, the cysteamine reducing agent is preferably the sole reducing agent, so the compositions are free of thio, sulfite, and other reducing agents.

The compositions of the invention may also contain a conditioning agent, generally about 0.1–10% by weight. The term "conditioning agent" in accordance with the invention means a compound or composition which exhibits a net positive charge and is capable of binding to the negative charged hair fibers. Most suitable are quaternary ammonium compounds, which are positively charged tetra-substituted nitrogen derivatives having the following formula:

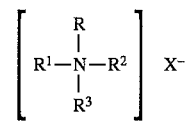

wherein R, $R^1$, $R^2$, and $R^3$ may be the same or different but may not be hydrogen; and wherein X- represents a typical anion such as methosulfate, chloride, etc. Suitable quaternary ammonium compounds of this formula are set forth on pages 41–42 of the C.T.F.A. Cosmetic Ingredient Handbook, First Edition, 1988, which is hereby incorporated by reference.

The composition of the invention may also contain 1–20%, preferably 2–10% of a moisturizing agent or humectant. The term "moisturizing agent" or "humectant" means a hygroscopic ingredient which reduces the evaporation of water. Examples of humectants include corn syrup, fructose, glucose, glycerin, glycol, 1,2,6-hexanetriol, honey, hydrogenated honey, hydrogenated starch hydrolysate, inositol, lactic acid, lactose, mannitol, $PEG_{4-200}$, PEG-5 pentaerythritol ether, polyglyceryl sorbitol, propylene glycol, sodium PCA, sorbitol, sucrose, urea, xylitol, acetamide MEA, glucamine, glucose glutamate, glucuronic acid, glutamic acid, glycereth, histidine, honey, maltitol, methyl gluceth, PCA, PEG-10 propylene glycol, polyamino sugar condensates, pyridoxine dilaurate, saccharide hydrolysate, sucrose, TEA-lactate, TEA-PCA, and mixtures thereof.

The composition of the invention may also include 0.01–5% of a chelating agent which acts to chelate the free iron or other metals which are often found in water. Suitable chelating agents include EDTA and derivatives thereof, HEDTA, citric acid, and those set forth on page 62 of the C.T.F.A. Cosmetic Ingredient Handbook, First Edition, 1988, which is hereby incorporated by reference.

Fragrance, other emulsifiers which aid in suspending the fragrance, may also be added to the composition of the invention.

Preferred compositions comprise:

12–18% cysteamine hydrochloride,

1–8% of a conditioning agent which is a cationic quaternary ammonium compound

2–10% of a moisturizing agent, and the remainder water.

The invention is also directed to a method for permanent waving human hair comprising the steps of:

(a) applying to hair fibers arranged in a predetermined configuration a permanent wave composition having a pH of 6.0 to 7.0 comprising 10–20% by weight of a cysteamine reducing agent in an aqueous carrier, (b) applying heat to the hair treated with the composition of (a) for a period of time sufficient to cause rupture of the sulfur to sulfur bonds in the hair fibers, (c) applying a neutralizer to the hair fibers for a period of time sufficient to cause the sulfur to sulfur bonds to reform.

Generally, the hair is first shampooed and wound into curlers or mandrels to set the hair into the desired configuration. The composition of the invention is applied to the hair and the individual is placed under a hair dryer, for example, to generate heat to move the reaction kinetics forward. The composition is left on the hair with the application of heat for a time appropriate to cause permanent waving of the hair. This time is either judged by the beauty operator, who will evaluate the condition of the patron's hair and make the appropriate judgement, or it can be determined by first doing a test curl to determine the optimum time. Generally the permanent wave composition will remain on the hair for approximately 10–55 minutes, preferably 15–45 minutes. The heat may be applied during the entire time the permanent wave composition is applied to hair, or for only part of the time. After the appropriate time period, the permanent wave composition is rinsed out of the hair with water and a neutralizing composition which is capable of reforming the sulfur to sulfur bonds is applied. A variety of neutralizing compositions is suitable, but hydrogen peroxide is the preferred neutralizing composition. The neutralizing composition is left on the hair for a period of time sufficient to cause reformation of the cystine sulfur to sulfur bonds, generally 2–25 minutes. The hair is then rinsed well to remove the neutralizing agent and the patron's permanent wave has been completed.

The invention is also directed to a kit for applying permanent waves to human hair comprising:

(a) a first container containing a permanent wave composition having a pH of 6.0 to 7.0 comprising 10–20% by weight of a cysteamine reducing agent compound in an aqueous carrier, and (b) a second container containing a neutralizer.

The first container is applied to the hair which has been configured in a predetermined shape. After a suitable time period, the hair is rinsed and the contents of the second container applied to the hair to cause reformation of the bonds which were broken due to the cysteamine reducing agent.

Most unexpectedly, the formula and process of the invention provides quality perming regardless of hair condition, and can be used on all types of hair with essentially equivalent results. In contrast, prior art formulations require the variation of reducing agent concentration, time, temperature, and pH to achieve perming of various types of hair. The formula of the invention most preferably requires the presence of heat because cysteamine does not readily reduce cystine in a non-alkaline environment.

The invention will be further described in connection with the following examples which are set forth for the purposes of illustration only.

EXAMPLE 1

A permanent wave composition was prepared as follows:

|  | w/w % |
|---|---|
| Water QS 100% |  |
| Cysteamine hydrochloride | 15.00 |
| Polyquatemium 6 | 2.78 |
| Pentasodium pentatate | 0.20 |
| Propylene glycol | 6.00 |
| Laureth-23 | 2.00 |
| Ammonium carbonate | 0.70 |
| Fragrance | 0.10 |

The pH of the composition was about 6.8 to 7.0.

We claim:

1. A method for permanent waving human hair comprising the steps of:

(a) applying to hair fibers arranged in a predetermined configuration a permanent wave composition having a pH of 6.5 to 7.0 comprising 12–18% by weight of a cysteamine reducing agent selected from the group consisting of cysteamine, cysteamine salt, and mixtures thereof in an aqueous carrier, (b) applying heat to the hair treated with the composition of (a) for 15 to 45 minutes, (c) rinsing the hair with water, and (d) applying hydrogen peroxide to the hair fibers for a period of time sufficient to cause the sulfur to sulfur bonds to reform.

2. The method of claim 1 wherein the reducing agent in the permanent wave composition is cysteamine hydrochloride.

3. The method of claim 1, wherein the permanent wave composition is free of thio or sulfite reducing agents.

4. The method of claim 1 wherein the cationic quaternary ammonium compound in the permanent wave composition is a positive charged tetra-substituted nitrogen derivative having the following formula:

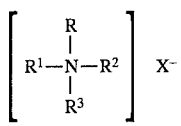

wherein R, $R^1$, $R^2$ and $R^3$ may be the same or different but may not be hydrogen, and wherein X-represents an anion.

5. The method of claim 4 wherein the cationic quaternary ammonium compound is Polyquaternium 6.

6. The method of claim 1 wherein the moisturizing agent is corn syrup, fructose, glucose, glycerin, glycol, 1,2,6-hexanetriol, honey, hydrogenated honey, hydrogenated starch hydrolysate, inositol, lactic acid, lactose, mannitol, $PEG_{4-200}$, PEG-5 pentaerythritol ether, polyglyceryl sorbitol, propylene glycol, sodium PCA, sorbitol, sucrose, urea, xylitol, acetamide MEA, glucamine, glucose glutamate, glucuronic acid, glutamic acid, glycerth, histidine, maltitol, methyl gluceth, PCA, PEG-10 propylene glycol, polyamino sugar condensates, pyridoxine dilaurate, saccaride hydrolysate, sucrose, TEA-lactate, TEA-PCA or mixtures thereof.

7. The method of claim 1 wherein the permanent wave composition additionally comprises 0.01–5% by weight of a chelating agent.

8. The method of claim 1 wherein the permanent wave compositions comprises:

12–18% of a cysteamine reducing agent selected from the group consisting of cysteamine, cysteamine hydrochloride, and mixtures thereof, 1–8% of a cationic quaternary ammonium compound conditioning agent, 2–10% of a moisturizing agent, and the remainder water.

9. A kit for application or permanent waves to human hair comprising:

(a) a first container containing a permanent wave composition free of thio or sulfite reducing agents having a pH of 6.0 to 7.0 comprising, by weight of the total composition, 10-20% by weight of a cysteamine reducing agent selected from the group consisting of cysteamine, a cysteamine salt, and mixtures thereof, 0.1–10% by weight of a conditioning agent which is a cationic quaternary ammonium compound, and 1–20% of a moisturizing agent, in an aqueous carrier, and (b) a second container containing a neutralizer which is hydrogen peroxide.

10. The kit of claim 9 wherein the cysteamine reducing agent is cysteamine hydrochloride.

11. The kit of claim 9 wherein the permanent wave composition comprises, by weight of the total composition:

(a) 12–18% of a cysteamine reducing agent selected from the group consisting of cysteamine, a cysteamine salt, and mixtures thereof, (b) 1–8% conditioning agent, (c) 2–10% moisturizing agent, and the remainder water.

12. The kit of claim 9 wherein the permanent wave composition additionally comprises 0.0 1–5% of a chelating agent.

13. The kit of claim 9 wherein the pH of the permanent wave composition is 6.5 to 7.0.

14. The kit of claim 9 wherein the cationic quaternary ammonium compound found in the permanent wave composition is a positively charged tetra-substituted nitrogen derivative having the following formula:

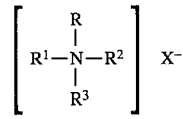

wherein R, $R^1$, $R^2$, and $R^3$ may be the same or different but may not be hydrogen, and wherein X-represents an anion.

15. The kit of claim 14 wherein the cationic quaternary ammonium compound is Polyquaternium 6.

16. The kit of claim 9 wherein the moisturizing agent found in the permanent wave composition is corn syrup, fructose, glucose, glycerin, glycol, 1,2,6-hexanetriol, honey, hydrogenated honey, hydrogenated starch hydrolysate, inositol, lactic acid, lactose, mannitol, $PEG_{4-200}$, PEG-5 pentaerythritol ether, polyglyceryl sorbitol, propylene glycol, sodium PCA, sorbitol, sucrose, urea, xylitol, acetamide MEA, glucamine, glucose glutamate, glucuronic acid, glutamic acid, glycereth, histidine, maltitol, methyl gluceth, PCA, PEG-10 propylene glycol, polyamino sugar condensates, pyridoxine dilaurate, saccaride hydrolysate, sucrose, TEA-lactate, TEA-PCA or mixtures thereof.

17. The kit of claim 12 wherein the chelating agent is EDTA.

* * * * *